US011318124B2

(12) United States Patent
Jimbo (10) Patent No.: US 11,318,124 B2
(45) Date of Patent: May 3, 2022

(54) COMBINATION THERAPY OF AXL INHIBITOR AND EGFR TYROSINE KINASE INHIBITOR

(71) Applicant: DAIICHI SANKYO COMPANY, LIMITED, Tokyo (JP)

(72) Inventor: Takeshi Jimbo, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 0 days.

(21) Appl. No.: 16/497,140

(22) PCT Filed: Mar. 23, 2018

(86) PCT No.: PCT/JP2018/011560
§ 371 (c)(1),
(2) Date: Sep. 24, 2019

(87) PCT Pub. No.: WO2018/174219
PCT Pub. Date: Sep. 27, 2018

(65) Prior Publication Data
US 2020/0345709 A1    Nov. 5, 2020

(30) Foreign Application Priority Data
Mar. 24, 2017    (JP) .............................. JP2017-058858

(51) Int. Cl.
*A61K 31/444* (2006.01)
*A61P 35/00* (2006.01)
*A61K 31/506* (2006.01)

(52) U.S. Cl.
CPC .......... *A61K 31/444* (2013.01); *A61K 31/506* (2013.01); *A61P 35/00* (2018.01)

(58) Field of Classification Search
CPC ...... A61K 31/444; A61K 31/506; A61P 35/00
USPC ....................................................... 514/275
See application file for complete search history.

(56) References Cited

U.S. PATENT DOCUMENTS

| 10,442,797 B2 * | 10/2019 | Haginoya .................. A61P 1/16 |
| 11,208,403 B2 * | 12/2021 | Haginoya ............. C07D 409/14 |
| 2017/0183329 A1 | 6/2017 | Haginoya et al. |

FOREIGN PATENT DOCUMENTS

| CN | 104109151 | 10/2014 |
| EP | 3168219 A1 | 5/2017 |
| WO | 2016/006706 A1 | 1/2016 |
| WO | WO 2017/086831 | 5/2017 |

OTHER PUBLICATIONS

Gao; Expert Rev Anticancer Ther. 2016, 16(4), 383-90. doi: 10.1586/14737140.2016.1162103. Epub Mar. 21, 2016. (Year: 2016).*

Angelillo-Scherrer et al., "Deficiency or inhibition of Gas6 causes platelet dysfunction and protects mice against thrombosis," *Nature Medicine*, (2001), 7(2):215-221.
Berclaz et al., "Estrogen dependent expression of the receptor tyrosine kinase axl in normal and malignant human breast," *Annals of Oncology*, (2001), 12:819-824.
Chung et al., "Expression of the Proto-Oncogene Axl in Renal Cell Carcinoma," *DNA and Cell Biology*, (2003), 22(8):533-540.
Craven et al., "Receptor Tyrosine Kinases Expressed in Metastatic Colon Cancer," *Int. J. Cancer*, (1995), 60:791-797.
Cross et al., "AZD9291, an Irreversible EGFR TKI, Overcomes T790M-Mediated Resistance to EGFR Inhibitors in Lung Cancer," *Cancer Discovery*, (2014), 4:1046-1061.
Ham et al., "Two Cases of Small Cell Lung Cancer Transformation from EGFR Mutant Adenocarcinoma During AZD9291 Treatment," *Journal of Thoracic Oncology*, (2015), 11(1):e1-e4.
Ito et al., "Expression of the Axl Receptor Tyrosine Kinase in Human Thyroid Carcinoma," *Thyroid*, (1999), 9(6):563-567.
Jänne et al., "AZD9291 in EGFR Inhibitor-Resistant Non-Small-Cell Lung Cancer," *The N. Engl. J. Med.*, (2015), 372(18):1689-1699.
Kim et al., "Mechanisms of Acquired Resistance to AZD9291: A Mutation-Selective, Irreversible EGFR Inhibitor," *J. Thoracic Onc.*, (2015), 10(12):1736-1744.
Linger et al., "Taking aim at Mer and Axl receptor tyrosine kinases as novel therapeutic targets in solid tumors," *Expert Opin. Ther. Targets*, (2010), 14(10):1073-1090.
Lu et al., "Tyro-3 family receptors are essential regulators of mammalian spermatogenesis," *Nature*, (1999), 398:723-728.
Lu et al., "Homeostatic Regulation of the Immune System by Receptor Tyrosine Kinases of the Tyro 3 Family," *Science*, (2001), 293:306-311.
Ma et al., "T790M and acquired resistance of EGFR TKI: a literature review of clinical reports," *J. Thorac. Dis.*, (2011), 3:10-18.
Nakano et al., "Vascular Smooth Muscle Cell-derived, Gla-containing Growth-potentiating Factor for $Ca^{2+}$-mobilizing Growth Factors," *The Journal of Biological Chemistry*, (1995), 270(11):5702-5705.
Nemoto et al., "Overexpression of Protein Tyrosine Kinases in Human Esophageal Cancer," *Pathobiology*, (1997), 65:195-203.
O'Bryan et al., "axl, a Transforming Gene Isolated from Primary Human Myeloid Leukemia Cells, Encodes a Novel Receptor Tyrosine Kinase," *Molecular and Cellular Biology*, (1991), 11(10):5016-5031.
Planchard et al., "EGFR-independent mechanisms of acquired resistance to AZD9291 in EGFR T790M-positive NSCLC patients," *Annals of Oncology*, (2015), 26:2073-2078.
Quong et al., "Protein kinases in normal and transformed melanocytes," *Melanoma Research*, (1994), 4:313-319.

(Continued)

*Primary Examiner* — Daniel R Carcanague
(74) *Attorney, Agent, or Firm* — Fish & Richardson P.C.

(57) ABSTRACT

The present invention provides a medicament comprising a compound represented by general formula (1) which has Axl inhibitory activity, and an EGFR tyrosine kinase inhibitor in combination, and a method for treating cancer using this combination. The present invention provides an excellent medicament and method for treating cancer which is highly effective for inhibiting resistance to an EGFR tyrosine kinase inhibitor in cancer treatment, and causes less adverse reactions such as weight loss.

12 Claims, 2 Drawing Sheets

(56) References Cited

OTHER PUBLICATIONS

Sawabu et al., "Growth Arrest-Specific Gene 6 and Axl Signaling Enhances Gastric Cancer Cell Survival via Akt Pathway," *Molecular Carcinogenesis*, (2007), 46:155-164.

Son et al., "Gas6/Axl-PI3K/Akt pathway plays a central role in the effect of statins on inorganic phosphate-induced calcification of vascular smooth muscle cells," *European Journal of Pharmacology*, (2007), 556:1-8.

Sun et al., "Coexpression of growth arrest-specific gene 6 and receptor tyrosine kinases Axl and Sky in human uterine endometrial cancers," *Annals of Oncology*, (2003), 14:898-906.

Sun et al., "Coexpression of Gas6/Axl in Human Ovarian Cancers," *Oncology*, (2004), 66:450-457.

Yanagita et al., "Essential role of Gas6 for glomerular injury in nephrotoxic nephritis," *The Journal of Clinical Investigation*, (2002), 110(2):239-246.

English Translation of International Search Report dated Jun. 26, 2018, in PCT Application No. PCT/JP2018/011560, 1 page.

English Translation of Written Opinion dated Jun. 26, 2018, in PCT Application No. PCT/JP2018/011560, 6 pages.

English Translation of International Preliminary Report on Patentability dated Sep. 24, 2019, in PCT Application No. PCT/JP2018/011560, 7 pages.

European Office Action in EP Appln. No. 18770641.1, dated Jun. 14, 2021, 7 pages.

Jimbo et al., "DS-1205b, a novel selective inhibitor of AXL kinase, blocks resistance to EGFR-tyrosine kinase inhibitors in a non-small cell lung cancer xenograft model", Oncotarget, 2019, 10(50):5152-5167.

Taiwanese Office Action in TW Appln. No. 107109774, dated Dec. 15, 2021, 12 pages with English Translation.

European Search Report in EP Appln. No. 18770641.1, dated Aug. 7, 2020, 8 pages.

Chinese Office Action in CN Appln. No. 201880019391.8, dated Mar. 14, 2022, 12 pages with English Translation.

Japanese Office Action in JP Appln. No. 2019507004, dated Feb. 1, 2022, 8 pages with English Translation.

\* cited by examiner

COMBINATION THERAPY OF AXL INHIBITOR AND EGFR TYROSINE KINASE INHIBITOR

This application is a national stage application under 35 U.S.C. § 371 of International Application No. PCT/JP2018/011560, filed Mar. 23, 2018, entitled "COMBINATION THERAPY TECHNIQUE FOR AXL INHIBITORY AGENT AND EGFR TYROSINE KINASE INHIBITOR," which claims priority to Japanese Patent Application No. 2017-058858, filed Mar. 24, 2017.

TECHNICAL FIELD

The present invention relates to a medicament comprising a compound having Axl inhibitory activity and an epidermal growth factor receptor (EGFR) tyrosine kinase inhibitor in combination, and a method for treating cancer using this combination.

BACKGROUND ART

Axl is a receptor tyrosine kinase belonging to the Tyro3-Axl-Mer (TAM) receptor tyrosine kinase family whose ligand is Gas6 protein, a growth factor. The gene of this kinase was originally identified as a transforming gene in chronic myelogenous leukemia (Non Patent Document 1).

The Gas6/Axl signalling system has been reported to regulate diverse cellular responses such as cell survival, cell division, autophagy, cell migration, angiogenesis, platelet aggregation, and NK cell differentiation (Non Patent Document 2). Also, many reports show the overexpression of Axl in tissues of cancers such as primary colon cancer (Non Patent Document 3), gastric cancer (Non Patent Document 4), esophagus cancer (Non Patent Document 5), melanoma (Non Patent Document 6), ovary cancer (Non Patent Document 7), kidney cancer (Non Patent Document 8), endometrial cancer (Non Patent Document 9), and thyroid gland cancer (Non Patent Document 10). The presence of Axl has been found to be closely related to the lymph node involvement and stage of lung cancer and ER expression in breast cancer (Non Patent Document 11).

Axl has been further found to play a role in immunity (Non Patent Document 12), platelet functions (Non Patent Document 13), spermatogenesis (Non Patent Document 14), vascular calcification (Non Patent Document 15), thrombin-induced vascular smooth muscle cell (VSMC) proliferation (Non Patent Document 16), and various kidney diseases, for example, acute and chronic glomerulonephritis, diabetic nephropathy, and chronic allograft rejection (Non Patent Document 17). Axl inhibitors are expected to provide therapeutic benefits to many diseases including cancers (including solid tumors such as carcinoma and sarcoma, leukemia, and lymphoid malignant diseases) as well as vascular diseases (including, but not limited to, thrombosis, atherosclerosis, and restenosis), kidney diseases (including, but not limited to, acute and chronic glomerulonephritis, diabetic nephropathy, and graft rejection), and diseases in which the disorganized formation of blood vessels has serious consequences (including, but not limited to, diabetic retinopathy, retinopathy, psoriasis, rheumatoid arthritis, atheroma, Kaposi's sarcoma, and angioma).

The applicant has discovered a compound that provides a safer Axl-inhibiting compound having high inhibition specificity for Axl, or a therapeutic agent for a disease caused by Axl hyperfunction, a therapeutic agent for a disease associated with Axl hyperfunction, and/or a therapeutic agent for a disease involving Axl hyperfunction, e.g., an anticancer agent, containing the Axl-inhibiting compound (Patent Document 1). Data on combined use with the EGFR tyrosine kinase inhibitor erlotinib are also provided therein.

Meanwhile, osimertinib, also known as an EGFR tyrosine kinase inhibitor, has been reported to obtain a response rate of 61% in 127 persons positive for a T790M mutation among non-small cell lung cancer patients treated with other EGFR tyrosine kinase inhibitors, and is thus expected to have efficacy (Non Patent Documents 18 and 19). However, it is known that resistance such as a C797S mutation (Non Patent Document 20), HER2 gene amplification (Non Patent Document 21), and transformation into small-cell cancer (Non Patent Document 22) occurs in patients given osimertinib. A solution thereto is demanded.

CITATION LIST

Patent Document

Patent Document 1: International Publication No. WO2016/006706

Non Patent Documents

Non Patent Document 1: O' Bryan et al., Mol. Cell. Biol., 11, 5031 (1991)

Non Patent Document 2: Rachel M A Linger et al., Expert Opin. Ther. Targets, 14, 1073 (2010)

Non Patent Document 3: Craven et al., Int. J. Cancer, 60, 791 (1995)

Non Patent Document 4: Sawabu et al., Mol. Carcinog., 46, 155 (2007)

Non Patent Document 5: Nemoto et al., Pathobiology, 65, 195 (1997)

Non Patent Document 6: Quong et al., Melanoma Res., 4, 313 (1994)

Non Patent Document 7: Sun et al., Oncology, 66, 450 (2004)

Non Patent Document 8: Chung et al., DNA Cell Biol., 22, 533 (2003)

Non Patent Document 9: Sun et al., Ann. Oncol., 14, 898 (2003)

Non Patent Document 10: Ito et al., Thyroid, 9, 563 (1999)

Non Patent Document 11: Berclaz et al., Ann. Oncol., 12, 819 (2001)

Non Patent Document 12: Lu et al., Science, 293, 306 (2001)

Non Patent Document 13: Angelillo-Scherrer et al., Nat. Med., 7, 215 (2001)

Non Patent Document 14: Lu et al., Nature, 398, 723 (1999)

Non Patent Document 15: Son et al., Eur. J. Pharmacol., 556, 1 (2007)

Non Patent Document 16: Nakano et al., J. Biol. Chem., 270, 5702 (1995)

Non Patent Document 17: Yanagita et al., J. Clin. Invest., 110, 239 (2002)

Non Patent Document 18: N Eng. J. Med. 372 (18), 1689 (2015)

Non Patent Document 19: Cancer Discv., 4(9), 1046 (2014)

Non Patent Document 20: Ann Oncol., 26 (10), 2073 (2015)
Non Patent Document 21: J. Thorac Oncol., 10 (12), 1736 (2015)
Non Patent Document 22: J. Thorac Oncol., 11 (1), e1 (2016)

SUMMARY OF INVENTION

Technical Problem

The present invention provides a medicament comprising a compound having Axl inhibitory activity and an EGFR tyrosine kinase inhibitor in combination, and a method for treating cancer using this combination. The present invention provides an excellent medicament and method for treating cancer which is highly effective for inhibiting resistance to an EGFR tyrosine kinase inhibitor in cancer treatment, and causes less adverse reactions such as weight loss.

Solution to Problem

As a result of conducting diligent studies, the present inventors have found that a particularly excellent antitumor effect is obtained by using a compound represented by formula (1):

[Formula 1]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or a pharmaceutically acceptable salt thereof which has Axl inhibitory activity, and an EGFR tyrosine kinase inhibitor (preferably osimertinib or a pharmaceutically acceptable salt thereof) in combination. This finding has led to the completion of the present invention.

Specifically, the present invention relates to the following (1) to (18):

(1) A medicament for cancer treatment, wherein a compound of formula (1):

[Formula 2]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or a pharmaceutically acceptable salt thereof and an EGFR tyrosine kinase inhibitor are administered in combination.

(2) A medicament according to (1), wherein the compound of formula (1):

[Formula 3]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or the pharmaceutically acceptable salt thereof and the EGFR tyrosine kinase inhibitor are respectively contained as active ingredients in different formulations and administered at the same time or different times.

(3) A medicament according to (1), wherein the compound of formula (1):

[Formula 4]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or the pharmaceutically acceptable salt thereof and the EGFR tyrosine kinase inhibitor are contained in a single formulation.

(4) A medicament according to (1), wherein the compound of formula (1):

[Formula 5]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or the pharmaceutically acceptable salt thereof and the EGFR tyrosine kinase inhibitor are in the form of a kit formulation comprising the compound or the pharmaceutically acceptable salt thereof and the EGFR tyrosine kinase inhibitor.

(5) A method for treating a cancer, comprising administering a compound of formula (1):

[Formula 6]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or a pharmaceutically acceptable salt thereof and an EGFR tyrosine kinase inhibitor in combination.

(6) A treatment method according to (5), wherein the compound of formula (1):

[Formula 7]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or the pharmaceutically acceptable salt thereof and the EGFR tyrosine kinase inhibitor are respectively contained as active ingredients in different formulations and administered at the same time or different times.

(7) A treatment method according to (5), wherein the compound of formula (1):

[Formula 8]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or the pharmaceutically acceptable salt thereof and the EGFR tyrosine kinase inhibitor are contained in a single formulation.

(8) A treatment method according to (5), wherein the compound of formula (1):

[Formula 9]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] or the pharmaceutically acceptable salt thereof and the EGFR tyrosine kinase inhibitor are in the form of a kit formulation comprising the compound or the pharmaceutically acceptable salt thereof and the EGFR tyrosine kinase inhibitor.

(9) A medicament according to any one of (1) to (4), wherein the salt of the compound of formula (1):

[Formula 10]

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] is sulfate.

(10) A treatment method according to any one of (5) to (8), wherein the salt of the compound of formula (1):

[Formula 11]

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] is sulfate.

(11) A medicament according to any one of (1) to (4) and (9), wherein the EGFR tyrosine kinase inhibitor is osimertinib or a pharmaceutically acceptable salt thereof.

(12) A treatment method according to any one of (5) to (8) and (10), wherein the EGFR tyrosine kinase inhibitor is osimertinib or a pharmaceutically acceptable salt thereof.

(13) A medicament according to any one of (1) to (4), (9), and (11), wherein the cancer is selected from breast cancer, colon cancer, colorectal cancer, prostate cancer, lung cancer, gastric cancer, ovary cancer, endometrial cancer, kidney cancer, hepatocellular cancer, thyroid gland cancer, uterus cancer, esophagus cancer, osteosarcoma, skin cancer, glioblastoma, neuroblastoma, head and neck cancer, testicular tumor, blood cancer and pancreatic cancer.

(13a) A medicament according to any one of (1) to (4), (9), and (11), wherein the cancer is selected from breast cancer, colon cancer, colorectal cancer, prostate cancer, lung cancer, gastric cancer, ovary cancer, endometrial cancer, kidney cancer, hepatocellular cancer, thyroid gland cancer, uterus cancer, esophagus cancer, squamous cell cancer, leukemia, osteosarcoma, melanoma, glioblastoma, neuroblastoma, and pancreatic cancer.

(14) A treatment method according to any one of (5) to (8), (10), and (12), wherein the cancer is selected from breast cancer, colon cancer, colorectal cancer, prostate cancer, lung cancer, gastric cancer, ovary cancer, endometrial cancer, kidney cancer, hepatocellular cancer, thyroid gland cancer, uterus cancer, esophagus cancer, osteosarcoma, skin cancer, glioblastoma, neuroblastoma, head and neck cancer, testicular tumor, blood cancer and pancreatic cancer.

(14a) A treatment method according to any one of (5) to (8), (10), and (12), wherein the cancer is selected from breast cancer, colon cancer, colorectal cancer, prostate cancer, lung cancer, gastric cancer, ovary cancer, endometrial cancer, kidney cancer, hepatocellular cancer, thyroid gland cancer, uterus cancer, esophagus cancer, squamous cell cancer, leukemia, osteosarcoma, melanoma, glioblastoma, neuroblastoma, and pancreatic cancer.

(15) A medicament according to any one of (1) to (4), (9), and (11), wherein the cancer is a cancer having a mutation in the EGFR gene.

(16) A treatment method according to any one of (5) to (8), (10), and (12), wherein the cancer is a cancer having a mutation in the EGFR gene.

(17) A medicament according to (15), wherein the mutation in the EGFR gene is any one or more of exon19del, L858R and T790M.

(18) A treatment method according to (16), wherein the mutation in the EGFR gene is any one or more of exon19del, L858R and T790M.

Advantageous Effects of Invention

The present invention produces excellent properties in terms of rapid exertion of drug efficacy, sustained drug efficacy, physical stability, solubility, oral absorbability, concentrations in blood, cell membrane permeability, metabolic stability, tissue distribution, bioavailability (BA), drug interaction, toxicity, etc., and is useful as a method for treating cancer and/or an anticancer agent.

DESCRIPTION OF EMBODIMENTS

In the present invention, the compound of formula (1):

[Formula 12]

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide] is a compound of Example 34 of WO2016/006706. This compound or a pharmaceutically acceptable salt thereof can be produced by a method described in WO2016/006706 (WO2016/006706 is incorporated herein by reference in its entirety).

EGFR is a tyrosine kinase receptor that performs signal transduction by recognizing a factor involved in cell proliferation. EGFR resides on a cell membrane. Upon activation of this receptor, differentiation or proliferation of the cell occurs. This EGFR is found in many cells and becomes involved in malignant transformation, infiltration or metastasis through its overexpression or gene mutation. EGFR exhibits overexpression or gene mutation in cells of various cancers including non-small cell lung cancer and colorectal cancer so that the cancer cells actively proliferate. Furthermore, the cells overexpressing EGFR or having an EGFR gene mutation have been found to be highly metastatic as compared with other cells. In this context, the inhibition of EGFR tyrosine kinase phosphorylation can block the signal transduction necessary for the proliferation of cancer cells. This suppresses the proliferation of the cancer cells.

It is known with regard to the mutation in the EGFR gene that activation mutations such as a mutation of leucine at the 858th position of the encoded protein to arginine (L858R), a deletion mutation of exon 19 (exon19del), a mutation of glycine at the 719th position of the encoded protein to a different amino acid (G719X), and a mutation of leucine at the 861st position of the encoded protein to glutamine (L861Q) are found in non-small cell lung cancer and the like. It is known that a mutation of threonine at the 790th position of the encoded protein to methionine (T790M) occurs in cancers that have acquired resistance to so-called first-generation EGFR tyrosine kinase inhibitors such as gefitinib or erlotinib.

Specific examples of the EGFR tyrosine kinase inhibitor used in the present invention include osimertinib, gefitinib, erlotinib, lapatinib, and afatinib. Osimertinib is particularly preferred.

In the present invention, osimertinib is a compound of formula (2):

[Formula 13]

(2)

[N-(2-{[2-(dimethylamino)ethyl](methyl)amino}-4-methoxy-5-{[4-(1-methyl-1H-indol-3-yl)pyrimidin-2-yl]amino}phenyl)prop-2-enamide], and is also referred to as Tagrisso® or AZD9291. This compound can be produced by a method described in WO13014448.

In the present invention, each of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide and the EGFR tyrosine kinase inhibitor may be various pharmaceutically acceptable salts.

Examples of the salt can include: hydrohalides such as hydrochlorides and hydroiodides; inorganic acid salts such as nitrates, perchlorates, sulfates, and phosphates; lower alkanesulfonates such as methanesulfonates, trifluoromethanesulfonates, and ethanesulfonates; arylsulfonates such as benzenesulfonates and p-toluenesulfonates; organic acid salts such as formates, acetates, malates, fumarates, succinates, citrates, tartrates, oxalates, and maleates; amino acid salts such as ornithine salts, glutamates, and aspartates; alkali metal salts such as sodium salts, potassium salts, and lithium salts; alkaline earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethyl ammonium salts, and tris(hydroxymethyl)aminomethane salts.

The salt of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide is preferably sulfate.

The salt of osimertinib is preferably mesylate.

In the present invention, N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or the pharmaceutically acceptable salt thereof and the EGFR tyrosine kinase inhibitor may each exist in a free or solvate form. The compound or the pharmaceutically acceptable salt thereof and the EGFR tyrosine kinase inhibitor may each exist in a hydrate form, for example, by absorbing moisture in the air. Solvates are not particularly limited as long as the solvate is pharmaceutically acceptable. Specifically, a solvate is preferably a hydrate, an ethanol solvate, or the like. Also, the compound or the pharmaceutically acceptable salt thereof and the EGFR tyrosine kinase inhibitor may each be in an N-oxide form. These solvates, hydrates, and N-oxide forms are also included in the scope of the present invention.

N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or the pharmaceutically acceptable salt thereof and the EGFR tyrosine kinase inhibitor may each produce a stereoisomer depending on the structure thereof. The present invention includes all of these stereoisomers, and mixtures of any proportions of these stereoisomers. The term stereoisomer is as defined in 1996 IUPC, Pure and Applied Chemistry 68, 2193-2222. When each of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or the pharmaceutically acceptable salt thereof and the EGFR tyrosine kinase inhibitor is present as a tautomer, both the case where these tautomers are present in equilibrium and the case where a certain form is dominantly present are included in the scope of the present invention. The term tautomer refers to an isomer resulting from the shift of a proton of one atom in a molecule to a different atom.

N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or the pharmaceutically acceptable salt thereof and the EGFR tyrosine kinase inhibitor may each be a "pharmaceutically acceptable prodrug compound" that is converted to the desired compound by enzymatic oxidation, reduction, hydrolysis, etc., or by hydrolysis, etc., by gastric acid or the like, through reactions with an enzyme, gastric acid or the like under physiological conditions in vivo.

Examples of the prodrug include acylated, alkylated, or phosphorylated compounds.

The prodrugs of the compounds can be produced by methods known in the art. The prodrugs of the compounds also include compounds that are converted to the desired compound under physiological conditions as described in "Iyakuhin No Kaihatsu" [Development of Pharmaceuticals], Vol. 7, Bunshi Sekkei [Molecular Design], Hirokawa Shoten, 1990, pp. 163-198.

In the present invention, the terms "tumor" and "cancer" are used interchangeably. In the present invention, tumor, malignant tumor, cancer, malignant neoplasm, carcinoma, sarcoma, etc., are also collectively referred to as "tumor" or "cancer". The terms "tumor" and "cancer" also include pathological conditions that are sometimes classified into a premalignant stage, such as myelodysplastic syndrome.

In one aspect, the present invention relates to a medicament or a treatment method, wherein N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and an EGFR tyrosine kinase inhibitor are administered in combination.

In one aspect, the present invention relates to a medicament or a treatment method for cancer treatment, wherein N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and an EGFR tyrosine kinase inhibitor are administered in combination.

In the present invention, the phrase "administered in combination" for N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or the pharmaceutically acceptable salt thereof and the EGFR tyrosine kinase inhibitor means that it is assumed that both the drugs are administered in combination.

In the present invention, the "administration in combination" of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or the pharmaceutically acceptable salt thereof and the EGFR tyrosine kinase inhibitor means that both the drugs are incorporated into the body of a recipient over a given period. A formulation containing both the drugs in a single formulation may be administered, or the drugs may be prepared in separate formulations and separately administered. In the case of preparing separate formulations, the timing of their administration is not particularly limited. The separate formulations may be administered at the same time or may be administered at different times or on different days in a staggered manner. In the case of administering N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or the pharmaceutically acceptable salt thereof and the EGFR tyrosine kinase inhibitor at different times or on different days, the order of their administration is not particularly limited. Usually, these formulations are administered according to their respective administration methods. Therefore, these formulations may be administered in the same number of doses or may be administered in a different number of doses. Also, in the case of preparing separate formulations, the respective administration methods (administration routes) of the formulations may be the same as each other, or these formulations may be administered by different administration methods (administration routes). Both the drugs do not have to exist at the same time in the body and may be incorporated into the body over a given period (e.g., 1 month, preferably 1 week, more preferably a few days, even more preferably 1 day). One of the active ingredients may have disappeared from the body at the time of administration of the other active ingredient.

Examples of a dosage form of the medicament of the present invention include 1) administration of a single formulation comprising N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and an EGFR tyrosine kinase inhibitor, 2) concurrent administration through the same administration route of two formulations separately prepared from N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and an EGFR tyrosine kinase inhibitor, 3) administration in a staggered manner through the same administration route of two formulations separately prepared from N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and an EGFR tyrosine kinase inhibitor, 4) concurrent administration through different administration routes of two formulations separately prepared from N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and an EGFR tyrosine kinase inhibitor, and 5) administration in a staggered manner through different administration routes of two formulations separately prepared from N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and an EGFR tyrosine kinase inhibitor.

In the present invention, the two different formulations may be in the form of a kit comprising these formulations.

A medicament according to the present invention comprises N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide or a pharmaceutically acceptable salt thereof and/or an EGFR tyrosine kinase inhibitor and a pharmaceutically acceptable carrier and can be administered as various injections such as intravenous injections, intramuscular injections, or subcutaneous injections, or by various methods such as oral administration or transdermal administration. A pharmaceutically acceptable carrier means a pharmaceutically acceptable material (e.g., an excipient, a diluent, an additive, or a solvent) that is involved in the transport of the composition from an organ to another organ.

A formulation (e.g., oral formulation or injection) can be appropriately selected according to the administration method and prepared by methods conventionally used for preparing various formulations. Examples of oral formulations can include tablets, powders, granules, capsules, pills, troches, solutions, syrups, elixirs, emulsions, and oily or aqueous suspensions. The active ingredients in these formulations may be orally administered either in free forms or in salt forms. An aqueous formulation can be prepared by forming an acid adduct with a pharmaceutically acceptable acid or by forming an alkali metal salt such as sodium. In the case of an injection, a stabilizer, a preservative, a solubilizing agent, and the like may be used in the formulation. A solution that may contain these adjuvants, etc., may be stored in a container and then lyophilized, for example, to form a solid formulation to be prepared before use. One dose may be stored in one container, or multiple doses may be stored in one container.

Examples of solid formulations include tablets, powders, granules, capsules, pills, and troches. These solid formulations may contain pharmaceutically acceptable additives together with a compound of the present invention. Examples of additives include fillers, bulking agents, binders, disintegrants, dissolution promoters, wetting agents, and lubricants, which can be selected and mixed as necessary to prepare a formulation.

Examples of liquid formulations include solutions, syrups, elixirs, emulsions, and suspensions. Examples of additives include suspending agents and emulsifiers, which can be selected and mixed as necessary to prepare a formulation.

Examples of pharmaceutical materials can include, but are not limited to: amino acids such as glycine, alanine, glutamine, asparagine, arginine and lysine; antioxidants such as ascorbic acid, sodium sulfate and sodium bisulfite; buffers such as phosphate, citrate or borate buffers, sodium bicarbonate and Tris-HCl solutions; fillers such as mannitol and glycine; chelating agents such as ethylenediaminetetraacetic acid (EDTA); complexing agents such as caffeine, polyvinylpyrrolidine, β-cyclodextrin and hydroxypropyl-β-cyclodextrin; bulking agents such as glucose, mannose and dextrin; other carbohydrates such as monosaccharides and disaccharides; coloring agents; corrigents; diluents; emulsifiers; hydrophilic polymers such as polyvinylpyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid and hydrogen peroxide; solvents such as glycerin, propylene glycol and polyethylene glycol; sugar alcohols such as mannitol and sorbitol; suspending agents; surfactants such as sorbitan ester, polysorbates such as polysorbate 20 and polysorbate 80, triton, tromethamine, lecithin and cholesterol; stability enhancers such as sucrose and sorbitol; elasticity enhancers such as sodium chloride, potassium chloride, mannitol and sorbitol; transport agents; excipients; and/or pharmaceutical additives. The amount of these pharmaceutical materials added is preferably 0.01 to 100 times, particularly, 0.1 to 10 times the weight of the drug. The recipe of a preferred pharmaceutical composition in a formulation can be appropriately determined by those skilled in the art according to an applicable disease, an applicable administration route, etc.

An excipient or a carrier in a pharmaceutical composition may be liquid or solid. Appropriate excipients or carriers may be other materials usually used in injectable water, physiological saline, artificial cerebrospinal fluid, and parenteral administration. Neutral physiological saline or physiological saline containing serum albumin may be used as a carrier. The pharmaceutical composition can contain a Tris buffer of pH 7.0 to 8.5, an acetate buffer of pH 4.0 to 5.5, or a citrate buffer of pH 3.0 to 6.2. These buffers can also contain sorbitol or other compounds.

Preferred examples of osimertinib formulations include, but are not limited to tablets supplemented with D-mannitol.

The present invention can be used for treating cancer in mammals, particularly, humans. The dose and the dosing interval of the medicament of the present invention can be appropriately selected according to the judgment of a physician depending on the site of the disease and the height, body weight, sex, or medical history of the patient. When the medicament of the present invention is administered to a human, the dose is in the range of approximately 0.01 mg/kg body weight to approximately 500 mg/kg body weight per day, preferably approximately 0.1 mg/kg body weight to approximately 100 mg/kg body weight per day, with respect to one type of active ingredient. In administration to a human, the dose is preferably administered in either a single dose or two to four separate doses per day, and the administration is preferably repeated at appropriate intervals. The daily dose may exceed the aforementioned dose according to the judgment of a physician, if necessary. Preferably, osimertinib is orally administered at a dose of 80 mg once a day to an adult. This dose may be appropriately increased or decreased according to the state of the patient.

Preferably, gefitinib is orally administered at a dose of 250 mg once a day to an adult. This dose may be appropriately increased or decreased according to the state of the patient.

Preferably, erlotinib is orally administered at a dose of 100 to 150 mg once a day to an adult. This dose may be appropriately increased or decreased according to the state of the patient.

N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide is preferably administered at a dose of 100 mg to 1000 mg, more preferably 100 mg, 200 mg, 300 mg, 400 mg, 500 mg, 600 mg, 700 mg, 800 mg, 900 mg or 1000 mg, per day to an adult.

The type of cancer to be treated is not particularly limited as long as the cancer is confirmed to be sensitive to the combination therapy of the present invention. Examples thereof include breast cancer, colon cancer, prostate cancer, lung cancer (including small cell lung cancer and non-small cell lung cancer), gastric cancer, ovary cancer, cervical cancer, endometrial cancer, uterine body cancer, kidney cancer, hepatocellular cancer, thyroid gland cancer, esophagus cancer, osteosarcoma, skin cancer (including melanoma), glioblastoma, neuroblastoma, head and neck cancer, testicular tumor, colorectal cancer, blood cancer (including leukemia, malignant lymphoma, and multiple myeloma), retinoblastoma, and pancreatic cancer. Among them, a cancer having a mutation in the EGFR gene is preferred. A cancer having any one or more of L858R, exon19del, G719X, L861Q, T790M, and the like (preferably any one or more of exon19del, L858R and T790M) as the mutation in the EGFR gene is preferred. Also, inoperable or recurrent non-small cell lung cancer that is resistant to EGFR tyrosine kinase inhibitors and is positive for a T790M mutation in the EGFR gene and/or has a deletion mutation in the EGFR gene exon 19 is preferred.

Various reports on the relation of Axl to cancers have been made from the viewpoints of the inhibition of growth, the inhibition of metastasis, migration, or invasion, and the overcoming of drug resistance.

Axl dominant negative mutants have been reported to inhibit brain tumor growth (Vajkoczy et al., PNAS 2006, 103, 5799). Tumors in glioblastoma patient-derived tissues having the expression of Axl or the coexpression of Axl/Gas6 have been reported to grow significantly more rapidly and to render the lifetime of the patients short (Hutterer et al., Clin Cancer Res 14, 130 (2008)). Axl shRNA has been reported to inhibit the growth of breast cancer cells (Yi-Xiang et al., Cancer Res 68, 1905 (2008)). As is evident from these reports, Axl inhibitors are useful in the inhibition of cell growth in cancers.

On the other hand, Axl dominant negative mutants have been reported to inhibit cell migration and invasion (Zhang et al., Cancer Res 68, 1905 (2008); Vajkoczy et al., PNAS 103, 5799 (2006); and Holland et al., Cancer Res 65, 9294 (2005)). Axl shRNA has been reported to inhibit metastasis in vivo (Li et al., oncogene 28, 3442 (2009)). Anti-Axl antibodies and siRNA have been reported to inhibit tumor growth and metastasis in a mouse model (Li et al., Oncogene 28, 3442 (2009); Ye et al., Oncogene 29, 5254 (2010)). Axl has been reported to promote cell invasion (Tai et al., Oncogene 27, 4044 (2008)). R-428, an Axl inhibitor, has been reported to inhibit a diffusion model of metastatic breast cancer (Holland et al., Cancer Res 70, 1544 (2010)). Axl antibodies, Axl shRNA, and an Axl inhibitor NA80x1 have been reported to inhibit the migration and invasion of breast cancer cells (Yi-Xiang et al., Cancer Res 68, 1905 (2008)). Additionally, there have been a plurality of reports on the involvement of Axl in the metastasis and malignant progression of prostate cancer, spleen cancer, metastatic ovary cancer, thymic carcinoma, and the like. As is evident from these reports, Axl inhibitors are useful for, for example, inhibiting, treating, and preventing cancer metastasis, cell migration, and cell invasion.

Also, Axl inhibitors have been reported to overcome imatinib resistance in gastric cancer (Mahadevan et al., Oncogene 26, 3909 (2007)). Axl has been found to be induced in the resistance of acute myeloid leukemia to chemotherapeutic agents such as doxorubicin, VP16, and cisplatin (Hong et al., Cancer Letters 268, 314 (2008)). Axl is reportedly activated in lapatinib resistance in HER-2 positive breast cancer cells (Liu et al., Cancer Res 69, 6871 (2009)). Axl has been reported to participate in the PLX4032 (vemurafenib) resistance mechanism (Johannessen et al., Nature 468, 968 (2010)). Additionally, Axl has been reported to participate in resistance to temozolomide, carboplatin, and vincristine (AK Keeating et al., Mol Cancer Ther 9 (5), 1298 (2010)). As is evident from these reports, Axl inhibitors are useful in overcoming drug resistance, for example, overcoming resistance to various anticancer agents.

A medicament according to the present invention may be used in combination with an additional antitumor agent. Examples thereof include antitumor antibiotics, antitumor plant components, BRM (biological response modifiers), hormones, vitamins, antitumor antibodies, molecular target drugs, alkylating agents, antimetabolites, and other antitumor agents.

More specifically, examples of alkylating agents include: alkylating agents such as nitrogen mustard, nitrogen mustard N-oxide, bendamustine, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and others such as busulfan, improsulfan tosylate, temozolomide, and dacarbazine.

Examples of various antimetabolites include: purine antimetabolites such as 6-mercaptopurine, 6-thioguanine, and thioinosine; pyrimidine antimetabolites such as fluorouracil, tegafur, tegafur uracil, carmofur, doxifluridine, broxuridine, cytarabine, and enocitabine; and antifolates such as methotrexate and trimetrexate.

Examples of antitumor antibiotics include mitomycin C, bleomycin, peplomycin, daunorubicin, aclarubicin, doxorubicin, idarubicin, pirarubicin, THP-adriamycin, 4'-epidoxorubicin, epirubicin, chromomycin A3, and actinomycin D.

Examples of antitumor plant components and their derivatives include: vinca alkaloids such as vindesine, vincristine, and vinblastine; taxanes such as paclitaxel, docetaxel, and cabazitaxel; and epipodophyllotoxins such as etoposide and teniposide.

Examples of BRM include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethynyl estradiol, chlormadinone, mepitiostane, and medroxyprogesterone.

Examples of vitamins include vitamin C and vitamin A.

Examples of antitumor antibodies and molecular target drugs include trastuzumab, rituximab, cetuximab, panitumumab, nimotuzumab, denosumab, bevacizumab, infliximab, ipilimumab, nivolumab, pembrolizumab, avelumab, pidilizumab, atezolizumab, ramucirumab, imatinib mesylate, dasatinib, sunitinib, lapatinib, dabrafenib, trametinib, cobimetinib, pazopanib, palbociclib, panobinostat, sorafenib, crizotinib, vemurafenib, quizartinib, bortezomib, carfilzomib, ixazomib, midostaurin, and gilteritinib.

Examples of other antitumor agents include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, sizofiran, picibanil, procarbazine, pipobroman, neocarzinostatin, hydroxyurea, ubenimex, thalidomide, lenalidomide, pomalidomide, eribulin, tretinoin, and krestin.

EXAMPLES

The present invention will be specifically described with reference to the Examples illustrated below. However, the present invention is not limited by these Examples, and these Examples should not be construed as a limitation in any sense.

Figure 1:
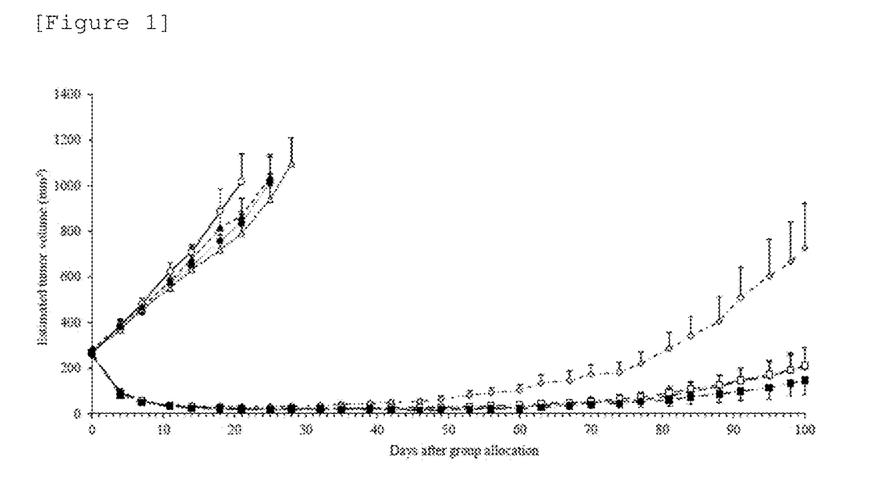
FIG. 1 is a diagram showing an in vivo effect brought about by combined use of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide sulfate hydrate (Compound A) and osimertinib on tumors derived from HCC827 lung cancer cells (which have a deletion mutation in the EGFR gene exon 19 and exhibit high sensitivity to EGFR inhibitors) subcutaneously transplanted in mice. The symbol open circle represents a group given a vehicle (0.5% MC). The symbol filled circle represents 12.5 mg/kg Compound A bid. The symbol open triangle represents 25 mg/kg Compound A bid. The symbol filled triangle represents 50 mg/kg Compound A bid. The symbol open rhomboid represents 3 mg/kg osimertinib qd. The symbol filled rhomboid represents 3 mg/kg osimertinib qd+12.5 mg/kg Compound A bid. The symbol open square represents 3 mg/kg osimertinib qd+25 mg/kg Compound A bid. The symbol filled square represents 3 mg/kg osimertinib qd+50 mg/kg Compound A bid. The ordinate depicts an estimated tumor volume calculated from tumor axes. The abscissa depicts the number of days after grouping. The error bar represents SE.
Figure 2:
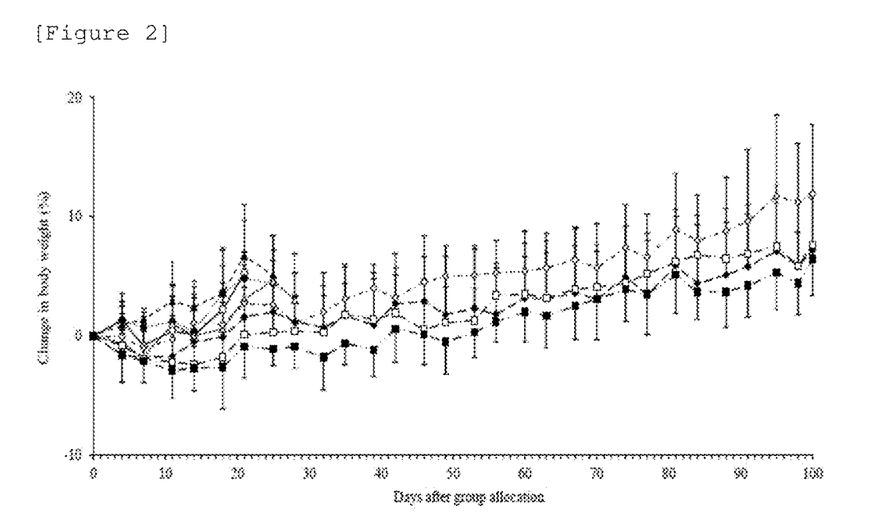
FIG. 2 is a diagram showing change in body weight when Compound A and osimertinib were administered in combination to tumors derived from HCC827 lung cancer cells (which have a deletion mutation in the EGFR gene exon 19 and exhibit high sensitivity to EGFR inhibitors) subcutaneously transplanted in mice. The symbol open circle represents a group given a vehicle (0.5% MC). The symbol filled circle represents 12.5 mg/kg Compound A bid. The symbol open triangle represents 25 mg/kg Compound A bid. The symbol filled triangle represents 50 mg/kg Compound A bid. The symbol open rhomboid represents 3 mg/kg osimertinib qd. The symbol filled rhomboid represents 3 mg/kg osimertinib qd+12.5 mg/kg Compound A bid. The symbol open square represents 3 mg/kg osimertinib qd+25 mg/kg Compound A bid. The symbol filled square represents 3 mg/kg osimertinib qd+50 mg/kg Compound A bid. The ordinate depicts the rate of change in body weight with respect to the body weight at the time of grouping. The abscissa depicts the number of days after grouping. The error bar represents SD.

Test Example 1: Study on In Vivo Effect Brought about by Combined Use of Compound A and Osimertinib Human non-small cell lung cancer-derived HCC827 cells having a deletion mutation in the EGFR gene exon 19 and exhibiting high sensitivity to EGFR inhibitors were suspended at $5 \times 10^7$ cells/mL in phosphate-buffered saline. 0.1 mL of the prepared cell suspension was subcutaneously transplanted to each nude mouse (female, 5 weeks old). When the mean estimated tumor volumes of the mice used reached 265.5 mm$^3$ (45 days after tumor transplantation), the mice were grouped according to their tumor volumes and forced to orally receive 3 mg/kg osimertinib (AZD9291; Shanghai Sun-shine Chemical Technology Co., Ltd) (once a day: qd) or 12.5, 25, or 50 mg/kg Compound A (twice a day: bid) (these agents were administered alone or in combination). The administration was started on the day (Day 1) following the grouping date and carried out five times a week (Saturday and Sunday were set to drug holidays). The administration was continued to Day 21 to Day 28 for the groups given a vehicle or Compound A alone, Day 100 for the group given osimertinib alone, and also Day 100 for the group given these agents in combination. The major axis (mm) and minor axis (mm) of each tumor were measured over time using an electronic digital caliper. The estimated tumor volume was calculated according to the expression (1) given below, and plotted. Also, the body weight was measured over time using an automatic balance for small animals. The rate of change in body weight (Change in body weight (%)) was calculated according to the expression (2) given below. In this way, the influence of drug administration on the body weight was studied, while the results of last body weight measurement were used in dose calculation.

$$\text{Estimated tumor volume (mm}^3\text{)} = \text{Mean estimated tumor volume of individuals per group} \quad (1)$$

$$\text{Estimated tumor volume of each individual} = An \times Bn^2/2$$

An: Major axis of the tumor at Day n
Bn: Minor axis of the tumor at Day n $$\text{Change in body weight (\%)} = \text{Mean rate of change in body weights of individuals per group} \quad (2)$$

$$\text{Rate of change in body weight of each individual} = (1 - BWn/BWs) \times 100$$

BWn: Body weight at Day n
BWs: Body weight at the initial day of administration

The results are shown in FIGS. 1 and 2 and Tables 1 and 2.

Osimertinib administered alone was confirmed to have a tumor regression effect immediately after administration. However, the tumor then acquired resistance and became bigger than its size at the start of administration at Day 81. By contrast, the tumor size in the group given osimertinib and Compound A in combination did not reach that at the start of administration even at Day 100 (final day), and the tumor thus exhibited no resistance (Table 1 and FIG. 1). No significant weight loss was found in the group given osimertinib and Compound A (Table 2 and FIG. 2), and no abnormal general symptom was found therein.

Thus, the combined use of Compound A and osimertinib according to the invention of the present application at any dose was confirmed to statistically significantly differ from the group given osimertinib alone at many points in time of observation. It was therefore able to be confirmed that this combined use is highly safe in spite of sustaining its effect for a long period and having a strong tumor regression effect.

TABLE 1

| | | Estimated tumor volume (mm³) | | | | | | | | |
|---|---|---|---|---|---|---|---|---|---|---|
| | No. of | Mean estimate tumor volume (mm³) | | | | | | | | |
| Group | animals | Day 0 | Day 4 | Day 7 | Day 11 | Day 14 | Day 18 | Day 21 | Day 25 | Day 28 |
| Vehicle control, bid | 5 | 265.0 | 390.1 | 483.0 | 626.7 | 709.3 | 887.1 | 1017.7 | — | — |
| Compound A 12.5 mg/kg, bid | 5 | 269.0 | 376.3 | 446.8 | 580.4 | 647.2 | 759.0 | 835.6 | 1013.6 | — |
| Compound A 25 mg/kg, bid | 5 | 273.7 | 366.6 | 458.8 | 550.8 | 631.7 | 718.2 | 792.0 | 939.4 | 1097.1 |
| Compound A 50 mg/kg, bid | 5 | 279.7 | 386.5 | 468.3 | 579.7 | 676.8 | 816.3 | 866.2 | 1037.5 | — |
| osimertinib 3 mg/kg, qd | 10 | 259.3 | 93.1 | 56.7 | 38.7 | 33.1 | 30.9 | 29.6 | 32.0 | 32.0 |
| osimertinib 3 mg/kg, qd + Compound A 12.5 mg/kg, bid | 10 | 257.1 | 96.7 | 55.6 | 33.5 | 30.5 | 24.6 | 20.1 | 21.9 | 22.1 |
| osimertinib 3 mg/kg, qd + Compound A 25 mg/kg, bid | 10 | 265.4 | 88.9 | 55.5 | 33.5 | 30.3 | 25.4 | 23.8 | 18.5 | 22.4 |
| osimertinib 3 mg/kg, qd + Compound A 50 mg/kg, bid | 10 | 267.8 | 80.5 | 49.3 | 31.0 | 24.8 | 20.7 | 17.5 | 17.3 | 17.8 |

| | No. of | Mean Estimated tumor volume (mm³) | | | | | | | | | |
|---|---|---|---|---|---|---|---|---|---|---|---|
| Group | animals | Day 32 | Day 35 | Day 39 | Day 42 | Day 46 | Day 49 | Day 53 | Day 56 | Day 60 | Day 63 | Day 67 |
| osimertinib 3 mg/kg, qd | 10 | 35.5 | 42.1 | 44.9 | 50.5 | 53.3 | 63.7 | 80.8 | 92.4 | 103.3 | 134.1 | 146.2 |
| osimertinib 3 mg/kg, qd + Counpoud A 12.5 mg/kg, bid | 10 | 21.4 | 22.0 | 23.2 | 20.9 | 20.2 | 22.3 | 25.8 | 25.1 | 28.5 | 37.6 | 40.4 |
| osimertinib 3 mg/kg, qd + Counpoud A 25 mg/kg, bid | 10 | 24.0 | 26.8 | 24.7 | 27.0 | 28.0 | 28.5 | 32.0 | 33.9 | 38.2 | 45.6 | 47.8 |
| osimertinib 3 mg/kg, qd + Counpoud A 50 mg/kg, bid | 10 | 16.5 | 18.7 | 19.4 | 18.5 | 14.2 | 15.7 | 19.3 | 22.6 | 21.7 | 28.1 | 34.9 |

TABLE 1-continued

Estimated tumor volume (mm³)

| Group | No. of animals | Mean estimated tumor volume (mm³) | | | | | | | | |
|---|---|---|---|---|---|---|---|---|---|---|
| | | Day 70 | Day 74 | Day 77 | Day 81 | Day 84 | Day 88 | Day 91 | Day 95 | Day 98 | Day 100 |
| osimertinib 3 mg/kg, qd | 10 | 171.8 | 182.1 | 220.1 | 286.7 | 341.2 | 404.1 | 509.3 | 602.4 | 665.6 | 727.5 |
| osimertinib 3 mg/kg, qd + Counpoud A 12.5 mg/kg, bid | 10 | 50.4 | 53.3 | 60.2 | 78.4 | 97.4 | 119.2 | 142.8 | 163.7 | 188.4 | 205.1 |
| osimertinib 3 mg/kg, qd + Counpoud A 25 mg/kg, bid | 10 | 54.4 | 64.9 | 73.1 | 91.6 | 108.6 | 126.8 | 146.1 | 172.4 | 191.9 | 211.3 |
| osimertinib 3 mg/kg, qd + Counpoud A 50 mg/kg, bid | 10 | 41.8 | 45.4 | 53.4 | 59.8 | 74.9 | 85.4 | 99.1 | 113.8 | 134.7 | 145.8 |

TABLE 2

Rate of change in body weight (%)

| Group | No. of animals | Mean change in body weight (%) | | | | | | | | |
|---|---|---|---|---|---|---|---|---|---|---|
| | | Day 0 | Day 4 | Day 7 | Day 11 | Day 14 | Day 18 | Day 21 | Day 25 | Day 28 |
| Vehicle control, bid | 5 | 0.0 | 1.3 | 0.8 | 0.4 | 0.1 | 2.2 | 5.3 | — | — |
| Compound A 12.5 mg/kg, bid | 5 | 0.0 | 1.3 | 0.7 | 1.2 | 0.4 | 3.6 | 4.8 | 4.4 | — |
| Compound A 25 mg/kg, bid | 5 | 0.0 | 0.6 | 1.8 | 1.0 | 0.0 | 0.6 | 3.1 | 4.6 | 3.0 |
| Compound A 50 mg/kg, bid | 5 | 0.0 | 0.9 | 1.4 | 2.9 | 2.4 | 3.6 | 6.7 | 5.1 | — |
| osimertinib 3 mg/kg, qd | 10 | 0.0 | 0.1 | 1.0 | 0.3 | 1.1 | 0.9 | 2.7 | 2.6 | 1.1 |
| osimertinib 3 mg/kg, qd + Compound A 12.5 mg/kg, bid | 10 | 0.0 | 1.6 | 1.8 | 71.7 | 0.5 | 0.1 | 1.6 | 2.0 | 1.2 |
| osimertinib 3 mg/kg, qd + Compound A 25 mg/kg, bid | 10 | 0.0 | 0.8 | 1.9 | 2.2 | 2.4 | 1.8 | 0.1 | 0.3 | 0.4 |
| osimertinib 3 mg/kg, qd + Compound A 50 mg/kg, bid | 10 | 0.0 | 1.6 | 2.1 | 2.9 | 2.7 | 2.6 | 0.9 | 1.1 | 0.9 |

| Group | No. of animals | Mean change in body weight (%) | | | | | | | | | |
|---|---|---|---|---|---|---|---|---|---|---|---|
| | | Day 32 | Day 35 | Day 39 | Day 42 | Day 46 | Day 49 | Day 53 | Day 56 | Day 60 | Day 63 | Day 67 |
| osimertinib 3 mg/kg, qd | 10 | 2.0 | 3.1 | 4.0 | 3.2 | 4.5 | 5.0 | 5.1 | 5.3 | 5.4 | 5.7 | 6.4 |
| osimertinib 3 mg/kg, qd + Compound A 12.5 mg/kg, bid | 10 | 0.7 | 1.7 | 0.9 | 2.7 | 2.9 | 1.8 | 2.3 | 1.8 | 3.2 | 3.1 | 3.6 |
| osimertinib 3 mg/kg, qd + Compound A 25 mg/kg, bid | 10 | 0.3 | 1.8 | 1.4 | 1.9 | 0.5 | 1.1 | 1.3 | 3.4 | 3.5 | 3.2 | 3.9 |
| osimertinib 3 mg/kg, qd + Compound A 50 mg/kg, bid | 10 | 1.8 | 0.6 | 1.2 | 0.6 | 0.1 | 0.5 | 0.3 | 1.2 | 2.0 | 1.7 | 2.5 |

| Group | No. of animals | Mean change in body weight (%) | | | | | | | | |
|---|---|---|---|---|---|---|---|---|---|---|
| | | Day 70 | Day 74 | Day 77 | Day 81 | Day 84 | Day 88 | Day 91 | Day 95 | Day 98 | Day 100 |
| osimertinib 3 mg/kg, qd | 10 | 5.7 | 7.4 | 6.6 | 8.9 | 8.0 | 8.8 | 9.6 | 11.7 | 11.2 | 11.9 |
| osimertinib 3 mg/kg, qd + Compound A 12.5 mg/kg, bid | 10 | 3.1 | 4.9 | 3.5 | 5.9 | 4.4 | 5.1 | 5.8 | 7.1 | 5.8 | 7.2 |
| osimertinib 3 mg/kg, qd + Compound A 25 mg/kg, bid | 10 | 4.1 | 4.4 | 5.2 | 6.2 | 6.8 | 6.5 | 6.9 | 7.5 | 5.9 | 7.6 |
| osimertinib 3 mg/kg, qd + Compound A 50 mg/kg, bid | 10 | 3.1 | 3.9 | 3.5 | 5.1 | 3.7 | 3.7 | 4.2 | 5.3 | 4.4 | 6.5 |

Figure 3:
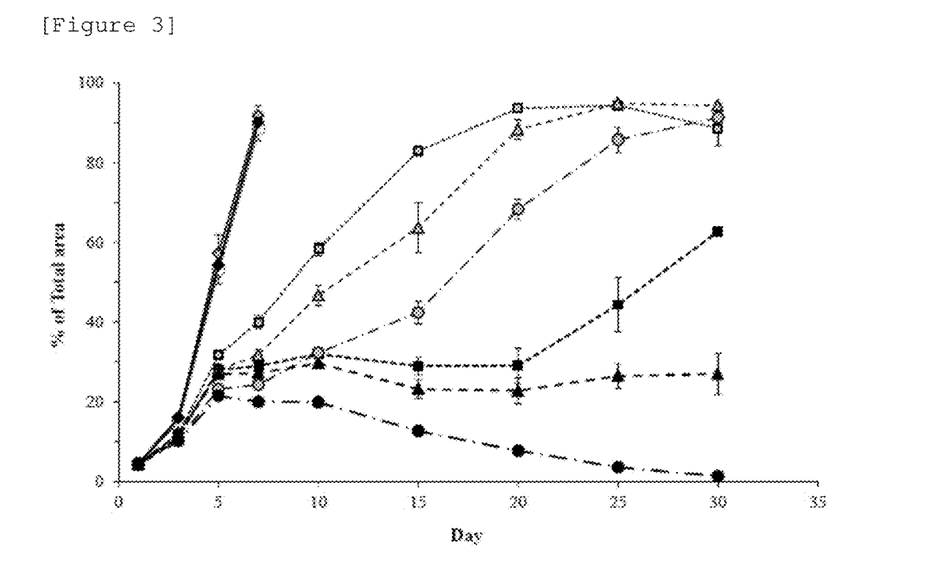
FIG. 3 is a diagram showing an effect brought about by combined use of Compound A and osimertinib on the in vitro proliferation of human non-small cell lung cancer-derived cells NCI-H1975 (which have a L858R mutation and a T790M mutation in the EGFR gene). The symbol open circle represents a vehicle. The symbol gray rhomboid represents 0.1 µM Compound A. The symbol filled rhomboid represents 1 µM Compound A. The symbol gray square represents 0.2 µM osimertinib. The symbol filled square represents 2 µM osimertinib. The symbol gray triangle represents 0.1 µM Compound A+0.2 µM osimertinib. The symbol filled triangle represents 0.1 µM Compound A+2 µM osimertinib. The symbol gray circle represents 1 µM Compound A+0.2 µM osimertinib. The symbol filled circle represents 1 µM Compound A+2 µM osimertinib. The error bar represents SD.

Test Example 2 Study on In Vitro Effect Brought about by Combined Use of Compound A and Osimertinib Human non-small cell lung cancer-derived NCI-H1975 cells having the EGFR gene mutations (L858R and T790M) were suspended in a medium (RPMI1640 medium containing 10% fetal bovine serum), inoculated ($1.5 \times 10^4$ cells/well) to each 12-well plate, and cultured overnight at 37° C. in the presence of 5% $CO_2$ in a humidified incubator. The supernatant was removed, and Compound A (final concentration: 0.1 or 1 µM) and osimertinib (AZD9291; Shanghai Sunshine Chemical Technology Co., Ltd) (final concentration: 0.2 or 2 µM) dissolved in DMSO and then diluted with a medium were added alone or in combination to each well. A medium containing 0.2% DMSO was added to control wells. The culture was continued at 37° C. in the presence of 5% $CO_2$ in a humidified incubator. The medium was replaced with a fresh one once every seven days.

The cells were stained at Day 1, Day 3, Day 5, Day 7, Day 10, Day 15, Day 20, Day 25, and Day 30 after the addition of the test compounds.

The cell staining, image analysis, and data analysis were performed by the following procedures.

The cells in the wells were fixed with 4% formaldehyde solution (room temperature, 25 min), reacted with PBS containing 0.1% Triton X-100 (room temperature, 15 min), and further stained at room temperature for 30 minutes by the addition of a staining solution (HCS CellMask Green/Hoechst 33342 mixed solution). Images were obtained using Array Scan VTI (Thermo Fisher Scientific Inc.) at 5× magnification of an objective lens and 100 obtained fields of view. Cell areas were analyzed using Cellomics View software. A cell occupancy rate per total photographed area was calculated with respect to each point of measurement according to the expression (1) given below. Also, the proliferation rate of the group treated with Compound A and osimertinib in combination with respect to the group treated with osimertinib alone was calculated according to the expression (2) given below using the mean cell occupancy rate of each group. A cell proliferation curve was prepared using the value of the cell occupancy rate (% of Total area).

Cell occupancy rate (%)={Area occupied by the cells ($m^2$)/Total photographed area (174493532 $µm^2$)}×100  (1)

Proliferation rate (%)=[{Mean cell occupancy rate (%) of the group treated with Compound A and osimertinib in combination}/{Mean cell occupancy rate (%) of the group treated with osimertinib alone}]×100  (2)

The results are shown in FIG. 3. The combined use of Compound A and osimertinib according to the invention of the present application was confirmed to also exhibit a significant antitumor effect on cancer cells having L858R and T790M (acquired mutations) mutations.

The invention claimed is:

1. A pharmaceutical composition, comprising a compound of formula (1):

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide], a pharmaceutically acceptable salt thereof, or a hydrate of the compound of formula (I) or a pharmaceutically acceptable salt thereof and an EGFR tyrosine kinase inhibitor;
wherein the EGFR tyrosine kinase inhibitor is osimertinib or a pharmaceutically acceptable salt thereof.

2. The composition of claim 1, wherein the compound of formula (1), or the pharmaceutically acceptable salt thereof, or the hydrate of the compound of formula (I) or the pharmaceutically acceptable salt thereof is a sulfate salt or a hydrate of the sulfate salt.

3. A kit comprising the composition of claim 1.

4. A method of treating a cancer, comprising administering to a patient in need thereof an effective amount of a compound of formula (1):

(1)

[N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide], a pharmaceutically acceptable salt thereof, or a hydrate of the compound of formula (I) or a pharmaceutically acceptable salt thereof and an EGFR tyrosine kinase inhibitor in combination;
   wherein the EGFR tyrosine kinase inhibitor is osimertinib or a pharmaceutically acceptable salt thereof;
   wherein the cancer is selected from the group consisting of breast cancer, colon cancer, colorectal cancer, prostate cancer, lung cancer, gastric cancer, ovary cancer, endometrial cancer, kidney cancer, heptocellular cancer, thyroid gland cancer, uterus cancer, esophagus cancer, osteosarcoma, skin cancer, glioblastoma, neuroblastoma, head and neck cancer, testicular tumor, blood cancer and pancreatic cancer.

5. The method of claim 4, wherein the compound of formula (1), the pharmaceutically acceptable salt thereof, or the hydrate of the compound of formula (I) or the pharmaceutically acceptable salt thereof and the EGFR tyrosine kinase inhibitor are separately contained in different formulations.

6. The method of claim 4, wherein the compound of formula (1), the pharmaceutically acceptable salt thereof, or the hydrate of the compound of formula (I) or the pharmaceutically acceptable salt thereof and the EGFR tyrosine kinase inhibitor are contained and administered in a single formulation.

7. The method of claim 4, wherein the compound of formula (1), or the pharmaceutically acceptable salt thereof, or the hydrate of the compound of formula (I) or the pharmaceutically acceptable salt thereof and the EGFR tyrosine kinase inhibitor are contained in and administered from a kit.

8. The method of claim 4, wherein the compound of formula (1), or the pharmaceutically acceptable salt thereof, or the hydrate of the compound of formula (I) or the pharmaceutically acceptable salt thereof is a sulfate salt or a hydrate of the sulfate salt.

9. The method of claim 4, wherein the cancer is a cancer having a mutation in the EGFR gene.

10. The method of claim 9, wherein the mutation in the EGFR gene is any one or more of exon19del, L858R and T790M.

11. The method of claim 8, wherein the cancer is a cancer having a mutation in the EGFR gene.

12. The method of claim 11, wherein the mutation in the EGFR gene is any one or more of exon19del, L858R and T790M.

* * * * *

UNITED STATES PATENT AND TRADEMARK OFFICE
CERTIFICATE OF CORRECTION

PATENT NO.       : 11,318,124 B2
APPLICATION NO.  : 16/497140
DATED            : May 3, 2022
INVENTOR(S)      : Takeshi Jimbo

Page 1 of 1

It is certified that error appears in the above-identified patent and that said Letters Patent is hereby corrected as shown below:

In the Claims

Column 28, Lines 10-32:

In Claim 1: delete "  " and insert

--.

Column 29, Line 13:
In Claim 4: delete "heptocellular" and insert -- hepatocellular --.

Signed and Sealed this
Twelfth Day of July, 2022

Katherine Kelly Vidal
Director of the United States Patent and Trademark Office